US005580392A

United States Patent [19]

Sulc et al.

[11] Patent Number: 5,580,392

[45] Date of Patent: Dec. 3, 1996

[54] CONTACT LENS CLEANING COMPOSITIONS WITH PARTICLES OF VARIABLE HARDNESS AND PROCESSES OF USE

[75] Inventors: Jiri S. Sulc, Newport Beach; Joseph E. Vigh, Placentia, both of Calif.

[73] Assignee: Allergan, Irvine, Calif.

[21] Appl. No.: 223,892

[22] Filed: Apr. 5, 1994

[51] Int. Cl.$^6$ .............................. B08B 3/08; B08B 3/04; C09G 1/04; A61K 9/16

[52] U.S. Cl. .............................. 134/7; 428/407; 428/403; 510/113

[58] Field of Search .............................. 134/7; 422/28, 422/30; 252/173, 174.13, 174.23, 174.24, 174.25, DIG. 2, DIG. 10, DIG. 14; 428/407, 403

[56] References Cited

U.S. PATENT DOCUMENTS

| | | | |
|---|---|---|---|
| 3,939,971 | 2/1976 | Tulis | 206/205 |
| 4,119,580 | 10/1978 | Smith, Jr. et al | 521/28 |
| 4,137,200 | 1/1979 | Wood et al. | 521/159 |
| 4,242,097 | 12/1980 | Rich, Jr. et al. | 422/70 X |
| 4,265,634 | 5/1981 | Pohl | 422/70 X |
| 4,269,306 | 5/1981 | Feniger | 206/5 |
| 4,314,823 | 2/1982 | Rich, Jr. et al. | 422/70 X |
| 4,351,909 | 9/1982 | Stevens | 521/28 |
| 4,376,047 | 3/1983 | Pohl | 428/402 X |
| 4,394,179 | 7/1983 | Ellis et al. | 134/7 |
| 4,455,233 | 6/1984 | Pohl | 422/70 X |
| 4,533,399 | 7/1985 | Mencke | 134/6 |
| 4,575,396 | 3/1986 | Matsumoto et al. | 134/7 |
| 4,655,957 | 4/1987 | Chromecek et al. | 252/174.23 |
| 4,767,559 | 8/1988 | Kruse et al. | 252/174.13 X |
| 4,779,300 | 10/1988 | Pompe | 15/104.93 |
| 4,826,658 | 5/1989 | Kay | 422/30 |
| 4,839,082 | 6/1989 | Bhatia | 252/174.23 X |
| 4,860,885 | 8/1989 | Kaufman et al. | 206/5.1 |
| 4,921,630 | 5/1990 | Bhatia | 252/174.23 X |
| 5,000,962 | 3/1991 | Sangekar et al. | 424/482 |
| 5,011,661 | 4/1991 | Schafer et al. | 422/30 |
| 5,037,484 | 8/1991 | Su et al. | 252/173 X |
| 5,054,610 | 10/1991 | Ajello | 206/5.1 |
| 5,088,146 | 2/1992 | Smith et al. | 15/104.94 |
| 5,089,053 | 2/1992 | Chou et al. | 134/7 |
| 5,089,240 | 2/1992 | Perlaky | 422/300 |
| 5,128,058 | 7/1992 | Ishii et al. | 252/174.13 |
| 5,190,760 | 3/1993 | Baker | 424/439 |
| 5,328,491 | 7/1994 | Yamada et al. | 44/280 |
| 5,401,327 | 3/1995 | Ellis et al. | 252/174.23 X |
| 5,461,433 | 10/1995 | Nakabayashi et al. | 252/174.23 X |
| 5,462,713 | 10/1995 | Schlitzer et al. | 422/37 |

FOREIGN PATENT DOCUMENTS

| | | |
|---|---|---|
| 0287189 | 10/1988 | European Pat. Off. . |
| 0415396 | 3/1991 | European Pat. Off. . |
| 5186791 | 7/1993 | Japan . |
| 8806073 | 7/1988 | WIPO . |

OTHER PUBLICATIONS

*Hackh's Chemical Dictionary,* 4th ed., ed. by Julius Grant, McGraw–Hill Book Company, 1969, p. 313.

*College Dictionary,* rev. ed. unabridged, ed. by Jess Stein, Random House, 1982, pp. 601–602.

*Primary Examiner*—Douglas J. McGinty

*Attorney, Agent, or Firm*—Frank J. Uxa

[57] ABSTRACT

Compositions and methods for treating a contact lens are disclosed. In one embodiment, the composition comprises an ophthalmically acceptable liquid aqueous medium and a plurality of particles which possess a hardness gradient. The hardness gradient of the particles is due to the particles having a relatively inelastic, water-impermeable core and a soft, water-permeable outer layer surrounding the core. The particles afford both high specific pressure on a contact lens surface and textural softness, which diminishes surface abrasion.

20 Claims, No Drawings

CONTACT LENS CLEANING COMPOSITIONS WITH PARTICLES OF VARIABLE HARDNESS AND PROCESSES OF USE

BACKGROUND OF THE INVENTION

The present invention relates to compositions and methods for treating, for example, cleaning, contact lenses. More particularly, the invention relates to particle-containing compositions useful for treating contact lenses, for example, to remove debris or deposit material from contact lenses.

Cleaning of contact lenses is desirable because of the tendency of material to deposit on the lenses. These deposits may include proteinaceous materials, lipids, as well as foreign matter, such as eye makeup, which can accumulate on the lens surface. Contact lens cleaning based solely on a chemical or solvent approach may have difficulty in affording deposit removal in a reasonable time and/or in removing all the deposit materials likely to be encountered. As an alternative, physically rubbing the lens with a cleaning composition may be advantageous.

A number of contact lens cleaning systems have been proposed which include a particulate component used to physically contact and clean contact lenses. For instance, Ishii et al, U.S. Pat. No. 5,128,058 describes a contact lens cleaner having microcapsules which reportedly assist in removing dirt or stains from a contact lens surface. The microcapsules are formed by laminating an inorganic polishing agent, such as silica, alumina, etc., onto a plastic core. A ball mill process is used whereby the inorganic agent is believed to adhere to the plastic due to frictionally generated electric charges on the plastic core. It is expected that the static electric charges which initially hold the laminated layer onto the plastic quickly dissipate, whereupon the formed particle either crumbles or stays together essentially as a plastic core surrounded by a substantially rigid inorganic shell. The outer shell of these particles is harder than the inner elastic core. It is likely that the hard outer surface of these particles disadvantageously causes significant scratching and/or wear of the contact lens surface coincident with removal of deposits from the surface.

Another cleaning agent proposed for use with hard and soft contact lenses is found in Suet al U.S. Pat. No. 5,037,484. This composition includes organic polymer or polysiloxane particles having a size between one and 600 microns suspended in a carrier, which usually contains a thickening agent. Due to the uniform elasticity or rigidity of these particles, depending upon the particular particle formation conditions, it is not likely that they can provide adequate scouring capacity when the particle is elastic or sufficient softness to avoid lens scratching when the particle is composed of a rigid polymer.

A further approach to a contact lens cleaning composition is proposed by Bhatia U.S. Pat. Nos. 4,921,630 and 4,839,082 which describe a chemical formulation that purportedly forms an abrasive precipitate, with or without the presence of an enzyme, upon the interaction of a carboxy vinyl polymer in the formulation with one or more substances on the surface of the lens. When an enzyme is present, the enzyme is believed to assist in the removal of protein deposits, and the like. It is difficult to control the formation and size of the precipitate particles to obtain adequate cleaning without damaging the lenses. The precipitate has uniform mechanical properties, for example, hardness and elasticity, throughout the particles.

Another cleaning composition that includes a particulate agent is described by Chromecek et al U.S. Pat. No. 4,655,957. This composition contains a particulate hydrophilic polymer or copolymer, which reportedly attracts lens deposits from the lens surface. These polymers are described as being in the form of solid beads. The composition, hardness and elasticity of the beads apparently can be modified with a "modulus modifier," which is added to the reaction mixture prior to bead formation and therefore is uniformly dispersed in the beads. Again, when a cleaning particle having an elastic surface is desired in order to avoid lens scratching, the entire particle must be elastic because of the bead formation process. This inherent property of these particles reduces their effectiveness in removing deposits from a lens surface.

It would be advantageous to provide an effective contact lens cleaning system which both effectively removes deposit material from the lenses and avoids detrimental abrasion or scratching of the lenses.

SUMMARY OF THE INVENTION

New compositions and methods for cleaning contact lenses have been discovered. The present compositions include particles having an effective hardness gradient, and preferably an effective elasticity gradient, which allows the compositions to be used, for example, by manually rubbing the particles on the surface of a contact lens, to effectively remove debris or deposit material from the contact lens substantially without detrimentally affecting the lens, such as by scratching or abrading the surface. The present invention allows the user to directly control the treating, for example, cleaning, of his/her contact lenses. Such direct control advantageously leads to enhanced user compliance and, ultimately, to enhanced ocular health. The present compositions can be made of readily available materials and can be very conveniently and relatively easily produced. The present methods are easily practiced and produce outstanding contact lens treating, for example, cleaning, results. In short, the present invention solves many of the problems noted above regarding prior contact lens cleaning systems.

In one broad aspect, the present invention is directed to compositions useful for treating, for example, cleaning, a contact lens. Such compositions comprise a liquid aqueous medium, such as an ophthalmically acceptable liquid aqueous medium, and a plurality of particles combined with, and preferably effective to absorb at least a portion of, the medium. Each particle is comprised of a relatively hard, preferably relatively inelastic, core surrounded by a softer, preferably more elastic, outer layer. That is, the core is harder, and preferably less elastic, than the outer layer. The present compositions preferably further comprise at least one additional component in an amount effective to provide a beneficial property to the lens being treated. For example, the composition may include a conventional wettability component effective to enhance the wettability of the treated lens and/or a conventional conditioning component effective to condition the treated lens. The added component or components are preferably combined with, for example, dissolved in, the liquid aqueous medium.

In a particularly useful embodiment, the present compositions further comprise an effective amount of a contact lens cleaning component. The cleaning component may be provided in the liquid aqueous medium which is preferably absorbed by the particles when they are admixed with medium.

In another broad aspect of the invention, methods for treating a contact lens are provided which employ the present compositions. The contact lens is contacted with the composition, preferably including a cleaning component, at conditions effective to provide the desired treatment of the lens, preferably to effect removal of deposit material from the lens. The contact lens is preferably manually rubbed with the composition. After this contacting, the lens may be rendered, for example, rinsed, free of the composition, if desired.

Without wishing to limit the invention to any particular theory of operation, it is believed that when a contact lens surface is cleaned using the present compositions, the relatively hard cores of the particles impart to the surface a specific pressure sufficient to dislodge deposit material therefrom. The soft outer layers of the particles, which directly contact the lens surface, act to reduce, or even eliminate, unwanted surface scratching and abrasion of the lens contacted with the particles. The outer layer also is believed to adhere or even bind physically or chemically to lens deposits, as by hydrogen bonding, thereby facilitating deposit material removal from the lens surface.

These and other aspects and advantages of the present invention will be apparent in the following detailed description and claims.

DETAILED DESCRIPTION OF THE INVENTION

The present invention is useful for treating a contact lens, preferably for cleaning a contact lens. Hard contact lenses, rigid gas permeable contact lenses and soft contact lenses can be treated in accordance with the present invention.

The present compositions comprise a liquid aqueous medium, for example, an ophthalmically acceptable liquid aqueous medium, and a plurality of particles combined or admixed with the liquid aqueous medium. A liquid aqueous medium or other material is said to be "ophthalmically acceptable" when it is compatible with ocular tissue, that is causes no significant or undue detrimental effect when brought into contact with ocular tissue. The plurality of particles in the composition are preferably effective to absorb at least a portion of the liquid aqueous medium with each particle thereby including water and any other soluble components present in the aqueous medium.

Each of the present particles has a core and an outer layer surrounding the core. The core is harder than the outer layer, for example, as can be determined by any conventional hardness measurement, such as a measurement system using the Rockwell hardness scale. The outer layer is preferably more elastic (has greater elasticity) than the core. This elasticity gradient can be determined using conventional techniques, for example, to compare the elasticity of the core material with the elasticity of the outer layer material.

The outer layer of the particles of the invention preferably has a porous structure and/or are able to absorb water when the particle is placed in contact with the liquid aqueous medium. The core is preferably less water permeable than is the outer layer. For example, the core may be substantially impermeable to water, in particular the present liquid aqueous medium and/or the outer layer of the particle may be highly water permeable. In one embodiment, the core has a potential water content, that is has the ability to absorb or otherwise combine and hold water, in an amount of 0% to about 20% by weight of the core. The outer layer has a potential water content of about 20% or about 30% to about 95% or more by weight of the outer layer. When the present particles take in water, they preferably swell or become bigger in size.

The present particles preferably have an internal potential water content gradient. That is, the relatively soft outer layer surrounding the core of the present particles preferably has a potential water content gradient, with the potential water content increasing in the direction from the core to the outer surface of the particles. The potential water content of the outer layer at the core, that is at the core/outer layer interface, of the particles preferably is in the range of about 0% to about 20% by weight and at the outer surface of the particles preferably is in the range of about 20% or about 30% to about 95% by weight.

The particles of the invention are preferably sized and adapted to be manually rubbed on a contact lens surface in order to effect the desired treatment of the lens. The present particles are preferably sufficiently large to be manually manipulated by a user but not so large that the particles become ineffective. The particle size is preferably in the range of about 0.1 micron to about 50 microns, more preferably about 0.2 micron to about 10 microns, in diameter. The particles are preferably provided in bead or substantially spherical form or in irregular particle form.

The present particles may be made of any suitable material provided that such particles function as described herein. The particles preferably comprise a polymeric material, and more preferably a hydrophilic polymeric material.

Suitable polymeric materials that can be used to form polymeric particles of the invention include, for example, polyolefins and polydiolefins such as polyethylene, polypropylene, polystyrene, polybutadiene and the like; nylon; polytetrafluoroethylene (PTFE); polyacrylates; polymethacrylates, such as polymethylmethacrylate (PMMA); acrylonitrile-butadiene-styrene (ABS) polymers; cellulosic polymers, such as ethyl cellulose and the like; polycarbonates, silicone polymers; polysulfones; and the like and mixtures thereof. Hydrophilic polymeric materials useful in the present particles preferably include a hydrophilic polymer derived from the monomeric component selected from olefins, in particular styrene, acrylic acid, acrylic acid esters, methacrylic acid, methacrylic acid esters, derivatives thereof and mixtures thereof.

In one embodiment, the particles comprise a hydrophilic polymeric material derived by modifying, for example, hydrophilizing, a hydrophobic polymeric material, such as by chemically modifying hydrophobic polymeric particles.

To illustrate such modification, substantially uniform polymeric particles are initially provided and are chemically treated to form the soft outer layer, of the particles of the present invention. For example, when a polymeric ester, such as PMMA, is used, a relatively soft outer layer can be generated by controlled or limited chemical reaction of the PMMA particles with an aqueous solution including a basic component, such as potassium hydroxide, to hydrolyze the ester. Such a procedure is particularly preferred because it increases the hydrophilicity of the polymer due to the formation of hydroxyl groups, as well as producing a relatively soft outer layer on the particles. The hydrolysis reaction should occur under controlled conditions so as to maintain the relatively hard cores of the particles, thereby achieving the desired hardness gradient in the particles.

Another suitable chemical reaction for forming the present hardness gradient particles involves sulfonation of aryl groups, such as are present in polystyrene. Thus, polystyrene particles are controllably reacted with an aqueous solution of sulfuric acid to sulfonate the aryl groups in the outer portion of the particles. This reaction results in forming particles derived from polystyrene which have relatively soft outer layers while the cores of the particles are maintained relatively hard. Preferably, this controlled chemical reaction is terminated before the aryl groups in the cores of the particles are sulfonated. The sulfonyl groups thereby placed on the aryl groups in the outer layer are hydrophilic, which accordingly increases the water content of the outer layers of the particles relative to the unmodified polystyrene cores of the particles.

Additional considerations regarding the above-described modification reactions, such as reaction temperature, reaction medium, reaction time, etc., are readily apparent to the skilled practitioner and depend, for example, upon the choice of polymer to be modified and the desired physical properties of the final particles.

In another embodiment, relatively hard particles, for example, made of polyethylene, polystyrene or the like, having diameters of about 5 or about 10 to about 50 microns are coated with much smaller particles, for example, having diameters of about 0.05 or about 0.1 to about 0.2 or about 0.5 micron, comprising sulfonated material, such as latex or the like material that have been functionally modified to contain sulfonate groups. These smaller particles may be either chemically, for example, covalently, or physically, for example, electrostatically, adhered to the larger particles. An example of such "coated" particles are those included in ion chromatography columns sold by Dionex Corporation under the trademark HPIC-AS4.

In a particularly useful embodiment, the outer layer of the present particles comprises an anionic material, for example, a polymer including anionic groups, such as cation exchange materials. Such anionic materials are believed to be effective in facilitating contact lens cleaning by binding lysozyme, a positively charged protein which is a substantial, even major, deposited material on most types of soft contact lenses.

Other hardness gradient particles suitable for use in the present invention include particles which have been used in surgical procedures.

The liquid media used are selected to have no substantial deleterious effect on the lens being treated, or on the wearer of the treated lens. The liquid media are constituted to permit, and even facilitate, the instant lens treatment or treatments. The liquid media are preferably aqueous-based and are preferably ophthalmically acceptable. In a particularly useful embodiment, the media are substantially isotonic liquid aqueous media. The liquid media preferably include an effective amount of a tonicity adjusting component to provide the liquid media with the desired tonicity. Particularly useful media are those derived from saline, e.g., a conventional saline solution, or buffered saline solution. The liquid aqueous media of the present invention preferably include a buffer component which is present in an amount effective to maintain the pH of the media in the desired range. Among the suitable buffer components or buffering agents that may be employed are those conventionally used in contact lens care products. Examples include citrates, borates, carbonates, bicarbonates, phosphates and the like. The buffer salts are preferably alkali metal, alkaline earth metal, or ammonium salts.

The liquid media are preferably substantially isopycnic with the particles. That is, it is preferred that the liquid medium used in any given composition have substantially the same density as the particles being employed. This feature facilitates the formation of the present compositions as stable, substantially uniform suspensions of particles in the liquid media in which vigorous mixing is not required before or during use. To achieve this substantial isopycncity, the liquid medium and particles are selected so that a substantial density match exists. In addition, the liquid medium and/or particles can be modified to achieve the desired isopycncity. For example, the density of the liquid medium can be modified by the addition of alcohols, such as isopropyl alcohol and/or the like materials, particularly when an aqueous-based liquid medium is employed.

The present compositions preferably further comprise at least one additional component in an amount effective to provide at least one beneficial property or effect to the lens being treated. The additional component is preferably combined with, for example, dissolved in, the liquid medium. Examples of suitable additional components include wettability components and/or conditioning components and/or lubricating components, such as polyvinylpyrrolidone, carboxymethyl cellulose, polyvinyl alcohol, hydroxypropylmethyl cellulose and the like.

The present compositions, with or without such additional components, are effective, for example, by being rubbed on the lens surface to remove, for example, physically remove, deposit material from the lens surface. If one or more additional components are included, the present compositions provide one or more beneficial properties to the treated lens, for example, making the lens more comfortable and/or safer to wear.

In a preferred embodiment, the present compositions further include an effective amount of a contact lens cleaning component. Such cleaning component at least facilitates, and preferably acts to effect, the removal of deposit material from a lens with which it is contacted.

When a cleaning component is included in the present compositions, the cleaning component is preferably present in an amount effective to remove debris or deposit material from the contact lens. Exemplary cleaning components include surfactants and enzyme components, such as those commonly employed to clean contact lenses.

Among the types of debris that form on contact lens during normal use are protein-based debris, mucin-based debris, lipid-based debris and carbohydrate-based debris. One or more types of debris may be present on a single contact lens.

Preferred nonionic surfactants for use in this invention include ethylene oxide/propylene oxide surfactants, for example, poloxamers and their block polymers of tetrafunctional initiators such as ethylenediamine and ethoxylated lauramide in concentrations ranging from 0.01% to 10% by weight of the composition. Additional nonionic surfactants include the polyethylene glycol esters of fatty acids (e.g., coconut, polysorbate), polyoxyethylene or polyoxypropylene ethers of higher alkanes ($C_{12}$-$C_{18}$). Other nonionic surfactants suitable for use can be readily ascertained, in view of the foregoing description, from McCutcheon's Detergents and Emulsifiers, North American Edition, McCutcheon Division, MC Publishing Co., Glen Rock, N.J. 07452, U.S.A. 1980.

The cleaning enzyme component employed may be selected from peroxide-active enzymes which are conventionally employed in the enzymatic cleaning of contact lenses. For example, many of the enzymes disclosed in Huth et al U.S. Reissue Pat. No. 32,672 and Karageozian et al U.S. Pat. No. 3,910,296 are useful in the present invention. These patents are incorporated in their entirety by reference herein.

Among the useful enzymes are those selected from proteolytic enzymes, lipases and mixtures thereof. Preferred proteolytic enzymes are those which are substantially free of sulfhydryl groups or disulfide bonds, whose presence may react with the active oxygen in the HPLM to the detriment of the activity of the enzyme. Metalloproteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Aspergillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down into two subclasses, subtilisin A and subtilisin B. In the subtilisin A grouping are enzymes derived from such species are *B. subtilis, B. licheniformis* and *B. pumulis*. Organisms in this sub-class produce little or no neutral protease or amylase. The subtilisin B sub-class is made up of enzymes from such organisms as *B. subtilis, B. subtilis subtills var. amylosacchariticus, B. amyloliquefaciens* and *B. subtilis* NRRL B3411. These organisms produce neutral proteases and amylases on a level comparable to their alkaline protease production. One or more enzymes from the subtilisin A sub-class are particularly useful.

In addition other preferred enzymes are, for example, pancreatin, trypsin, collagenase, keratinase, carboxylase, aminopeptidase, elastase, and aspergillipeptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3Anson units of activity, preferably about 0.01 to about 1 Anson units, per single lens treatment. Higher or lower amounts may be used.

Enzyme activity is pH dependent, so for any given enzyme, there is a particular pH range in which that enzyme will function best. The determination of such range can readily be done by known techniques.

Preservatives, stabilizers, sequestering agents, thickening agents and/or the like materials conventionally used in contact lens care products may be employed in the present compositions in effective amounts to provide a desired benefit to the present composition and/or the contact lens being treated and/or to the wearer of the treated lens. Selecting which of these components and the amounts or concentrations of such components to employ in the present compositions will be apparent to the skilled practitioner. Because the present particles preferably swell in the presence of the liquid aqueous medium, thickening agents may not be needed or desired in the present compositions.

The present methods comprise contacting a contact lens to be treated with a composition of the invention. The contacting step can include, for example, one or more of such actions including pouring, immersing, covering and/or otherwise touching a composition to a surface of the lens at conditions to effect the desired treating, for example, cleaning, of the lens. Such contacting step preferably includes manually rubbing the contact lens with the present composition. Such contacting step may involve abrading debris from the lens surface as well as binding deposit material on the lens through the interactions of the soft outer layer of the present particles, whereby such outer layer temporarily adheres to the deposit material.

The temperature at which the contacting occurs may be selected so as to maintain the liquid aqueous medium in the liquid state, for example, in the range of about 0° C. to about 100° C., preferably in the range of about 10° C. to about 50° C. Contacting at room temperature is very convenient and provides very good results. The contacting may occur for times in the range of about 0.1 minutes to about 3 minutes or about 5 minutes or more. Such times are particularly advantageous when the contacting comprises manually rubbing the present composition on a contact lens surface. It is contemplated that a contact lens treating procedure in accordance with the present invention preferably comprises rinsing and/or otherwise rendering the lens substantially free of the present composition, for example, the particles of the present composition.

Incident with the above-described compositions are method for making the compositions. Such methods comprise providing a plurality of particles as described above, and combining the particles with a liquid aqueous medium.

A preferred method of preparing the compositions further comprises combining a plurality of such particles, the liquid aqueous medium and contact lens cleaning component and/or one or more other additional components.

The following non-limiting examples illustrate certain aspects of the present invention:

EXAMPLE 1

Polymethylmethacrylate (PMMA) beads having an average diameter of about 5 microns are conventionally prepared.

These beads are then contacted with an aqueous solution containing potassium hydroxide. This contacting occurs at conditions effective to hydrolyze the beads to a limited extent. Thus, a major portion of the PMMA polymer at or near the outer surface of the beads is hydrolyzed whereas little or no hydrolysis occurs at the center or core of the beads. The degree of hydrolysis decreases in a direction from the outer surface of the beads to the inner core of the beads.

After this controlled hydrolysis reaction, the treated beads are washed with water to remove residual potassium hydroxide and are vacuum dried. These dried beads are found to have an inner core which is quite hard and a softer outer layer surrounding this core. The outer layer has a substantial degree of hydrophilicity which decreases from the outer surface to the inner core of the beads.

EXAMPLE 2

Polystyrene beads having a average diameter of about 5 microns are conventionally prepared.

A mass of these polystyrene particles are contacted with an aqueous solution of sulfuric acid at conditions effective to sulphonate the polystyrene to a limited extent. After this controlled reaction, the sulfuric acid is neutralized with a aqueous solution of sodium hydroxide. The resulting treated polystyrene beads are washed with water and vacuum dried. The treated polystyrene beads are found to have a relatively hard inner core surrounded by a softer outer layer. The outer layer has significant hydrophilicity, whereas the inner core has relatively little hydrophilicity. The controlled sulfonation results in a gradient of hydrophilicity decreasing in a direction from the outer surface of the treated beads to the inner core of the treated beads.

EXAMPLE 3

An aqueous solution is prepared, by blending the various components together and has the following composition:

| | |
|---|---|
| $Na_2HPO_4$ | 5.0 grams |
| $Na_2EDTA$ | 5.5 grams |
| Conventional Nonionic Surfactants | 15.0 grams |
| Distilled Water | Q.S to 1 liter |

The treated beads produced in Example 1 are suspended in the above-noted solution so that the suspension contains about 5% by weight of such beads. In the presence of this formulation, the beads swell, and are found to have absorbed some of the solution.

A quantity of this suspension is used to clean a debris laden contact lens. The suspension is placed on the contact lens at room temperature (22° C.) and is manually rubbed on the surface of the lens for one (1) minute.

As a result of this rubbing, debris is removed from the contact lens and no abrasion of the lens surface occurs. The cleaned lens is rinsed with a buffered saline solution and placed in the eye for safe and comfortable wear.

EXAMPLE 4

Example 3 is repeated except that the aqueous solution contained up to 20% by volume of isopropyl alcohol sufficient to render the solution isopycnic with the suspended particles.

As a result of the rubbing, debris is removed from the contact lens and no abrasion of the lens surface occurs. The cleaned lens is rinsed with a buffered saline solution and placed in the eye for safe and comfortable wear.

EXAMPLES 5 and 6

Separate quantities of the treated beads produced in Example 2 are suspended in the aqueous solutions identified in Examples 3 and 4 so that the suspensions contain about 5% by weight of such beads. The treated particles swell in the presence of the solutions and are found to have absorbed some of the solutions.

Each of these suspensions is used to clean a debris laden contact lens. The suspension is placed on the contact lens at room temperature (22° C.) and is manually rubbed on the surface of the lens for one (1) minute.

As a result of each of these contactings, debris is removed from the contact lens without adversely affecting, for example, without abrading or scratching, the lens surface. In each case, the cleaned lens is rinsed in a buffered saline solution and placed in the eye for safe and comfortable wear.

EXAMPLE 7

An aqueous contact lens cleaning composition is prepared having the following composition:

| | |
|---|---|
| $Na_2HPO_4$ | 5.0 grams |
| $Na_2EDTA$ | 5.5 grams |
| Subtilisin A | 50 Anson Units |
| Distilled Water | QS to 1 liter |

A suspension of the treated beads produced in Example 1 and the above-noted composition is prepared so that the suspension includes 5% by weight of these beads.

This suspension is used to clean a debris laden contact lens. Thus, at room temperature (22° C.), a quantity of the suspension is manually rubbed on the surface of the contact lens for one (1) minute to remove debris therefrom. It is found that the suspension is effective to remove debris from the contact lens without causing any detrimental effect to the lens. The cleaned lens is rinsed free of the suspension using a buffered saline solution. The cleaned lens is then placed in the eye for safe and comfortable wear.

EXAMPLE 8

A suspension of the composition identified in Example 5 and the treated beads of Example 2 is produced so that these beads comprise 5% by weight of the suspension.

This suspension is used to clean a debris laden contact lens. At room temperature (22° C.), the suspension is manually rubbed on the surface of the contact lens for one (1) minute and debris is removed from the lens. It is found that the suspension is effective to remove debris without causing any detrimental effect to the contact lens. The cleaned lens is rinsed free of the suspension with a buffered saline solution and then placed in the eye for safe and comfortable wear.

The present invention is very effective in cleaning contact lenses of proteinaceous and other types of debris material. The physical rubbing of the present compositions on the surfaces of the lenses facilitates this cleaning, particularly when a contact lens cleaning component is included. Importantly, this physical rubbing or scouring is effective to clean the lens without causing harm to the lens. The hardness gradient of the present particles is effective to protect the lens against harm while, at the same time, providing sufficient pressure on the lens surface to facilitate removing the deposit material. The present compositions and methods are relative straightforward and easy to produce and practice, and result in substantial contact lens treating benefits.

While this invention has been described with respect to various specific examples and embodiments, it is to be understood that the invention is not limited thereto, and that it can be variously practiced within the scope of the following claims.

What is claimed is:

1. A composition useful for treating a contact lens comprising:

an ophthalmically acceptable liquid aqueous medium; and a plurality of particles combined with said ophthalmically acceptable liquid aqueous medium and being sized and adapted to be manually rubbed on the contact lens to effect the treating of the contact lens, each of said particles having a core including a first polymeric material and an outer layer including a second polymeric material surrounding said core, and said outer layer is more elastic than said core.

2. The composition of claim 1 wherein said particles are effective to absorb at least a portion of said ophthalmically acceptable liquid aqueous medium.

3. The composition of claim 1 further comprising an effective amount of a contact lens cleaning component.

4. A composition useful for cleaning a contact lens comprising:

a liquid aqueous medium;

an effective amount of a contact lens cleaning component; and a plurality of particles combined with said liquid aqueous medium and being sized and adapted to be manually rubbed on a contact lens to effect the cleaning of the contact lens, each of said particles having a core including a first polymeric material and an outer layer including a second polymeric material which surrounds said core, and said outer layer is more elastic than said core.

5. The composition of claim 4 wherein said particles are effective to absorb at least a portion of said liquid aqueous medium.

6. A method for cleaning a contact lens comprising manually rubbing said contact lens with the composition of claim 4.

7. The composition of claim 1 wherein said second polymeric material is a hydrophilic polymeric material.

8. The composition of claim 7 wherein said hydrophilic polymeric material comprises a hydrophilized polymeric material.

9. The composition of claim 7 wherein said hydrophilic polymeric material includes a hydrophilic polymer derived from a monomeric component selected from the group consisting of styrene, acrylic acid, acrylic acid esters, methacrylic acid, methacrylic acid esters, derivatives thereof and mixtures thereof.

10. A method for treating a contact lens comprising contacting said contact lens with the composition of claim 1.

11. A method for cleaning a contact lens comprising contacting said contact lens with the composition of claim 3.

12. The method of claim 11 wherein said contacting includes manually rubbing said contact lens with said composition.

13. The method of claim 12 further comprising rendering said contact lens substantially free of said composition.

14. The composition of claim 4 wherein said second polymeric material is a hydrophilic polymeric material.

15. The composition of claim 14 wherein said hydrophilic polymeric material comprises a hydrophilized polymeric material.

16. The composition of claim 14 wherein said hydrophilic polymeric material includes a hydrophilic polymer derived from a monomeric component selected from the group consisting of styrene, acrylic acid, acrylic acid esters, methacrylic acid, methacrylic acid esters, derivatives thereof and mixtures thereof.

17. The method of claim 6 which further comprises rendering said contact lens substantially free of said composition.

18. The composition of claim 7 wherein said core has a potential water content in the range of about 0% to about 20% by weight and said outer layer has a potential water content in the range of about 30% to about 95% by weight.

19. The composition of claim 18 wherein each of said particles has a diameter in the range of about 0.1 micron to about 50 microns.

20. The composition of claim 14 wherein said core has a potential water content in the range of about 0% to about 20% by weight and said outer layer has a potential water content in the range of about 30% to about 95% by weight, and each of said particles has a diameter in the range of about 0.1 micron to about 50 microns.

* * * * *